United States Patent
Park

(10) Patent No.: US 9,427,363 B2
(45) Date of Patent: Aug. 30, 2016

(54) PAD COATED WITH COFFEE

(71) Applicant: Sam Mun Park, Seoul (KR)

(72) Inventor: Sam Mun Park, Seoul (KR)

( * ) Notice: Subject to any disclaimer, the term of this patent is extended or adjusted under 35 U.S.C. 154(b) by 0 days.

(21) Appl. No.: 14/415,138

(22) PCT Filed: Jul. 15, 2013

(86) PCT No.: PCT/KR2013/006307
§ 371 (c)(1),
(2) Date: Jan. 16, 2015

(87) PCT Pub. No.: WO2014/014244
PCT Pub. Date: Jan. 23, 2014

(65) Prior Publication Data
US 2015/0190290 A1   Jul. 9, 2015

(30) Foreign Application Priority Data
Jul. 16, 2012  (KR) .................... 10-2012-0077115

(51) Int. Cl.
| | | |
|---|---|---|
| *A61F 13/15* | (2006.01) | |
| *A61F 13/84* | (2006.01) | |
| *A61F 13/472* | (2006.01) | |
| *A61L 15/46* | (2006.01) | |
| *A61L 15/40* | (2006.01) | |
| *A61F 13/51* | (2006.01) | |

(52) U.S. Cl.
CPC ......... *A61F 13/8405* (2013.01); *A61F 13/472* (2013.01); *A61L 15/40* (2013.01); *A61L 15/46* (2013.01); *A61F 2013/51076* (2013.01); *A61F 2013/8408* (2013.01); *A61F 2013/8435* (2013.01)

(58) Field of Classification Search
CPC ............ A61F 13/472; A61F 13/8405; A61F 2013/51076; A61F 2013/8408; A61F 2013/8435
See application file for complete search history.

(56) References Cited

U.S. PATENT DOCUMENTS

| | | | | |
|---|---|---|---|---|
| 3,939,838 | A  * | 2/1976 | Fujinami | ................. A61L 15/46 604/359 |
| 8,440,138 | B1 * | 5/2013 | Standifer | ............. A43B 1/0045 36/44 |
| 2003/0041808 | A1 * | 3/2003 | Wulforst | ............. A01K 1/0353 119/28.5 |

FOREIGN PATENT DOCUMENTS

| | | |
|---|---|---|
| JP | 2005-065750 A1 | 3/2005 |
| KR | 10-492750 B1 | 6/2005 |
| KR | 10-2012-0026324 A1 | 3/2012 |

* cited by examiner

*Primary Examiner* — Bradley Philips
(74) *Attorney, Agent, or Firm* — John K. Park; Park Law Firm

(57) ABSTRACT

Disclosed herein is a pad coated with coffee which includes: an outer cover which comes into direct contact with the vagina of a woman; a coating layer which is formed below the outer cover and smells of coffee; an absorber which is laid below the coating layer to absorb secretions; and a waterproof outer cover which is laid below the absorber to prevent the secretions absorbed into the absorber from leaking out, wherein coffee powder is coated on the coating layer.

2 Claims, 4 Drawing Sheets

PAD COATED WITH COFFEE

BACKGROUND OF THE INVENTION

1. Field of the Invention

The present invention relates to a pad coated with coffee, and more particularly, to a pad coated with coffee which includes: an outer cover which comes into direct contact with the vagina of a woman; a coating layer which is formed below the outer cover and smells of coffee; an absorber which is laid below the coating layer to absorb secretions; and a waterproof outer cover which is laid below the absorber to prevent the secretions absorbed into the absorber from leaking out, wherein coffee powder is coated on the coating layer.

2. Background Art

In general, a sanitary pad means a pads used when a woman menstruates, and recently, mugwort steam pads or fomentation pads which have heating packs attached to one side of each sanitary pad are increasing in use, together with the sanitary pads.

Such sanitary pads are mainly used when women menstruate, but the mugwort steam pads or the fomentation pads are used beyond the menstruation period. However, Korean Patent Laid-open No. 10-1999-0064932 discloses a disposable diaper or pad containing charcoal, and FIG. 1 illustrates the disposable diaper or sanitary pad disclosed in Korean Patent Laid-open No. 10-1999-0064932.

The sanitary pad disclosed in Korean Patent Laid-open No. 10-1999-0064932 includes a liquid penetrable cover 1; a water absorbable body 2 formed in the cover 1; and an airpermeable cover 3 which is disposed in the water absorbable body 2 and contains charcoal therein. However, the sanitary pad disclosed in Korean Patent Laid-open No. 10-1999-0064932 has several disadvantages in that it is not easy to put the charcoal 4 inside the airpermeable cover 3 and form the water absorbable body 2 outside the airpermeable cover 3 and in that the diaper or pad is increased in volume because relatively large amount of charcoal are needed to provide deodorizing effects.

Korean Patent No. 10-0492750 discloses a sanitary pad containing a functional composition, and FIG. 2 illustrates the sanitary pad containing the functional composition.

The sanitary pad disclosed in Korean Patent No. 10-0492750 includes: an outer cover 10 which comes into direct contact with the vagina of a woman; an absorber 20 of which the upper surface is coated with menstruated blood absorbing substance 25; and a waterproof outer cover 30 for preventing the menstruated blood absorbed into the absorber 20 from leaking out, wherein the menstruated blood absorbing substance 25 coated on the upper side of the absorber 20 contains a high molecular absorber and an oriental medicine composite including 16.5 to 18.5 wt % of mugwort, 9 to 11 wt % of cnidum, 6.5 to 8.5 wt % of dong quai, 4 to 6 wt % of mint and 9 to 11 wt % of starch. However, in a case of the oriental medicine composite, persons who dislike the smell of oriental medicines avoid use of the disclosed sanitary pad because the oriental medicine composite contained in the sanitary pad redolent with oriental medicines.

In the meantime, coffee is widely used as an air freshener in vehicles or sealed spaces and is known as deodorant for a refrigerator or known to provide a good effect if grounds of brewed coffee are put in an ash tray in order to remove the smell of smoke.

SUMMARY OF THE INVENTION

Accordingly, the present invention has been made to solve the above-mentioned problems occurring in the prior arts, and it is an object of the present invention to provide a pad coated with coffee which provides the aroma of coffee which makes a favorable impression to the public because coffee having a deodorizing effect is directly coated on a sanitary pad or a mugwort steam pad.

To accomplish the above object, according to the present invention, there is provided a pad coated with coffee including: an outer cover which comes into direct contact with the vagina of a woman; a coating layer which is formed below the outer cover and smells of coffee; an absorber which is laid below the coating layer to absorb secretions; and a waterproof outer cover which is laid below the absorber to prevent the secretions absorbed into the absorber from leaking out, wherein coffee powder or coffee extract is coated on the coating layer.

The pad coated with coffee according to the present invention can remove a bad smell by secretions, makes even users who dislike the smell of oriental medicines use the pad without avoidance and provides effects helpful to human bodies through intrinsic functions of coffee because the pad is coated with coffee.

BRIEF DESCRIPTION OF THE DRAWINGS

The above and other objects, features and advantages of the present invention will be apparent from the following detailed description of the preferred embodiments of the invention in conjunction with the accompanying drawings, in which.

BEST MODE

Figure 1:
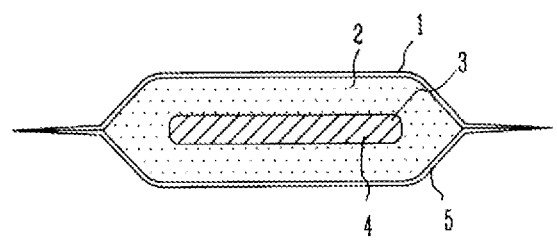
FIGS. 1 and 2 are views showing a structure of a sanitary pad according to a prior art.
Figure 2:
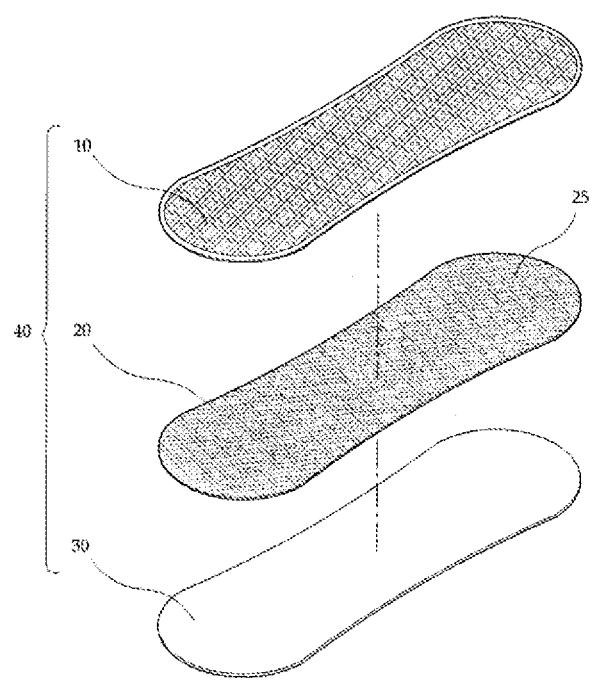

The present invention relates to a pad coated with coffee, and more particularly, to a pad coated with coffee which includes: an outer cover which comes into direct contact with the vagina of a woman; a coating layer which is formed below the outer cover and smells of coffee; an absorber which is laid below the coating layer to absorb secretions; and a waterproof outer cover which is laid below the absorber to prevent the secretions absorbed into the absorber from leaking out, wherein coffee powder is coated on the coating layer.

The pad coated with coffee according to the present invention which is used as hygienic goods includes: an outer cover 10 which comes into direct contact with the vagina of a woman; a coating layer 15 which is formed below the outer cover 10 and smells of coffee; an absorber 20 which is laid below the coating layer 15 to absorb secretions; and a waterproof outer cover 30 which is laid below the absorber 20 to prevent the secretions absorbed into the absorber 20 from leaking out. Coffee powder 16 is coated on the coating layer 15, and the coffee powder 16 is produced through the step of pulverizing dried coffee beans in 50 mesh size or less and is coated on the coating layer 15 together with an adsorbing material in order to enhancing an adhesive strength of the coating layer 15, thereby removing the smells of secretions and providing intrinsic functions of coffee so as to be helpful to human bodies.

The pad coated with coffee according to the present invention which is used as hygienic goods includes: an outer cover 10 which comes into direct contact with the vagina of a woman; an absorber 20 which is laid below the outer cover 10 to absorb secretions; and a waterproof outer cover 30 which is laid below the absorber 20 to prevent the secretions absorbed into the absorber 20 from leaking out. Coffee powder 16 is coated on the absorber 20, and the coffee powder 16 is produced through the step of pulverizing dried coffee beans in 50 mesh size or less and is coated on the coating layer 15 together with an adsorbing material in order to enhancing an adhesive strength of the coating layer 15, thereby removing the smells of secretions and providing intrinsic functions of coffee so as to be helpful to human bodies.

MODE FOR INVENTION

Hereinafter, reference will be made in detail to the preferred embodiments of the present invention with reference to the attached drawings.

Figure 3:
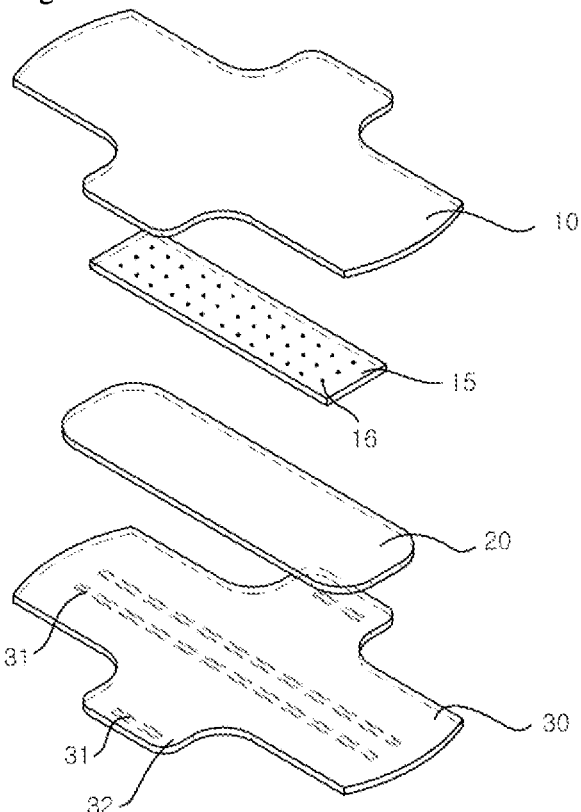
FIG. 3 is a view showing a structure of a pad coated with coffee according to a preferred embodiment of the present invention.

FIG. 3 is a view showing a structure of a pad coated with coffee according to a preferred embodiment of the present invention. The pad coated with coffee according to the present invention includes: an outer cover 10 which comes into direct contact with the vagina of a woman; a coating layer 15 which is formed below the outer cover 10 and smells of coffee; an absorber 20 which is laid below the coating layer 15 to absorb secretions; and a waterproof outer cover 30 which is laid below the absorber 20 to prevent the secretions absorbed into the absorber 20 from leaking out. Coffee powder 16 is coated on the coating layer 15, and the coffee powder 16 is produced through the step of pulverizing dried coffee beans in 50 mesh size or less and is coated on the coating layer 15 together with an adsorbing material in order to enhancing an adhesive strength of the coating layer 15, thereby removing the smells of secretions and providing intrinsic functions of coffee so as to be helpful to human bodies.

The unexplained reference numeral 31 designates an adhesion part, and 32 designates a wing part.

First, the outer cover 10 may be a surface layer having a plurality of pores to absorb secretions, and the absorber 20 may be made of a liquid absorbable material which can absorb secretions of high molecular materials. Moreover, the waterproof outer cover 30 may be made with a polyethylene coating film.

The coffee powder 16 or coffee extracts may be coated on the coating layer 15, and the coffee powder 16 is produced through the step of finely pulverizing dried coffee beans and is coated on the coating layer 15 as it is. The coffee extracts may be produced through the steps of: boiling coffee in water and drying and pulverizing essence of the boiled coffee.

In a case that the coffee powder 16 is coated on the coating layer 15, the coffee powder 16 which is pulverized in 50 mesh size or less is directly coated on the coating layer 15 or, if it is worried about agglutination of coffee powder, at least one among Elvan, germanium, fertile soil, red clay, charcoal, kelp powder and tourmaline is mixed with the coffee powder 16 and the mixture is coated on the coating layer 15. In order to enhance an adhesive force of the coating layer 15, the coffee powder 16 may be coated on the coating layer 15 after an adsorbing material is spread on the coating layer 15.

In the above-mentioned embodiment, the coating layer 15 is formed on the upper side of the absorber 20, but of course, the coating layer 15 can be formed beneath the absorber 20 or in the middle of the absorber 20.

In the meantime, it is known that coffee has various effects of preventing gastric cancer and liver cancer, strengthening of blood pressure, enhancing calculation ability, losing weight, preventing hangover after drinking and removing bad breath.

In connection with prevention of gastric cancer, researchers (Dakejaki Tosiro, et. al.) of Aichi Cancer Center Laboratory in Japan said that persons who had a habit of drinking three or more cups of coffee everyday halved in ratio of getting gastric cancer in comparison with persons who drank two or less cups of coffee through an epidemiologic investigation performed to about 20,000 persons. As described above, the reason why coffee reduces the ratio of getting gastric cancer is that antioxidant materials contained in coffee restrain generation of cancer cells and the Western style dietary life that persons who enjoy coffee likes provides an effect of preventing gastric cancer.

In connection with liver cancer, researchers (Dokui Noritaka, et. al.) of Sangyo College of Medicine in Japan investigated liver cancer prevention effects of coffee to 7,000 persons. Through the investigation, it was presented that persons who frequently drink coffee were reduced to 30% in death rate by liver cancer compared with persons who did not drink coffee.

In connection with strengthening of blood pressure, till now, people thought that coffee increases blood pressure because blood pressure temporarily rises when a person drinks coffee. However, researchers (Wakabayashi Kaos, et. al.) of Hoi College of Medicine in Japan surveyed relationship between a habit of drinking coffee and blood pressure to about 4,000 middle-aged men. As a result of the survey, it was known that persons who enjoy coffee are lower in blood pressure than persons who do not drink coffee. According to the survey, it was revealed that the maximum blood pressure decreased 0.6 mmHg and the minimum blood pressure decreased 0.4 mmHg when the persons drank a cup of coffee every day and that the degree that the blood pressure decreased was proportional to an increase of the number of times of drinking coffee every day.

In connection with enhancement of calculation ability, many people experienced that foods with caffeine clear the head and enhance the efficacy of work. Researchers think caffeine has an action to activate nerves. Caffeine of 120 to 200 mg (one or two cups of coffee) a day acts over the length and breadth of cerebral cortex to enhance thinking skills and clears the head to enable persons actively do intellectual work.

In connection with losing weight, coffee help losing weight by promoting metabolism. The reason is that a person who takes caffeine is increased in calorie intake by 0.1 percent even though persons eat the same foods because caffeine increases an energy consumption rate by about 10 percent, thereby preventing obesity. Caffeine converts subcutaneous fat into energy earlier than glycogen.

In connection with prevention of hangover after drinking, hangover is caused because alcohol is decomposed in the body and converted into acetaldehyde and acetaldehyde remains in the body for a long time. Caffeine activates liver functions to promote decomposition of acetaldehyde and activates movement of the kidney to promote excretion. When a person drinks coffee with a cup of water after drinking, it is a great help of removal of hangover.

In connection with removal of bad breath, furan contained in coffee has a function to remove bad smells. Besides the above effects, it is known that coffee has various effects, such as treatment of depression, prevention of colorectal cancer, improvement of endurance. Especially, coffee is very effective in removing of the smell of garlics.

The pad coated with coffee according to the present invention can provide various effects including deodorizing effects because coffee is coated on the coating layer of the pad.

Figure 4:
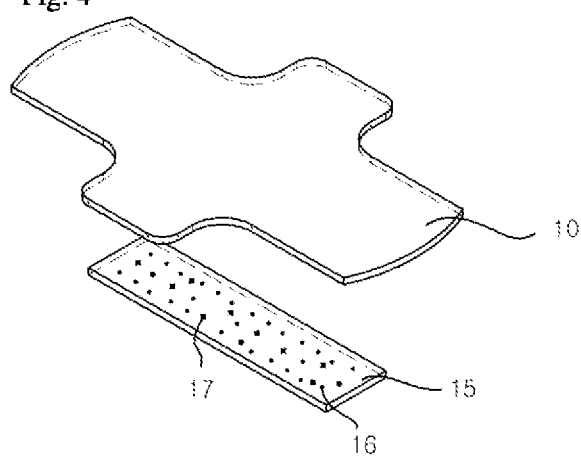
FIG. 4 is a view of a pad coated with coffee according to another preferred embodiment of the present invention.

FIG. 4 is a view showing a pad coated with coffee according to another preferred embodiment of the present invention. Fruit powder 17 together with coffee powder 16 is coated on the pad.

For the fruits, which are easy to be obtained and are inexpensive, there are lemons, Japanese apricots, strawberries, bananas, apples, quinces, peaches, apricots, pomegranates, oranges, grapefruits, kiwis, tomatoes, grapes, tangerines, pears, pineapples, persimmons and so on.

First, lemons are rich in vitamin C and controls sebum secretion so as to adjust rough skin texture, promote metabolism to control balance of skin nutrition and prevent oxidation and inflammation of the skin. Furthermore, lemons is effective to prevent propagation of germs and remove fishy smells, such that the pad can prevent propagation of germs on the pad when lemons are added to the coating layer.

Next, Japanese apricots remove dead cells to make the skin clean and bright and provide an antiallergic action by making protein of animals as antigens and a sterilizing action, such that the pad can prevent propagation of germs on the pad when Japanese apricots are added to the coating layer.

Next, strawberries contains lots of vitamin C so as to activate the function of the adrenal cortex which controls various hormones and enhance physical strength, such that the pad is effective to control hormones when strawberries are added to the coating layer.

Next, bananas are good to patients who have heart diseases or kidney troubles and who have to take a little sodium because bananas are low in fat and sodium and are also good to persons who have gastroenteric troubles or symptoms of diarrhea because sugar contained in bananas digests easily.

The present invention is not to directly take such fruits, but can enhance deodorization of secretions because the smell of bananas is very familiar to people Apples and peaches contain pectin between a fruit and the fruit's skin so as to provide anti-cancer effect and analgesic effect, such that the pad is effective in menstrual pain when apples and peaches are added to the coating layer.

The pad according to the present invention can remove bad smells due to secretions by emitting the fruit smells of fruit extracts or fruit powder and the smell of coffee.

Figure 5:
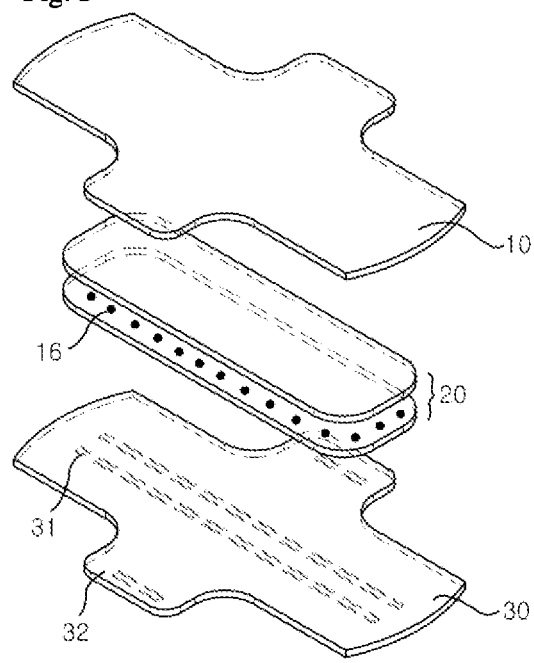
FIGS. 5 to 7 are views of a pad coated with coffee according to a further preferred embodiment of the present invention.

FIG. 5 is a view showing a pad coated with coffee according to a further preferred embodiment of the present invention. The pad coated with coffee according to the present invention which is used as hygienic goods, includes: an outer cover 10 which comes into direct contact with the vagina of a woman; an absorber 20 which is laid below the outer cover 10 to absorb secretions; and a waterproof outer cover 30 which is laid below the absorber 20 to prevent the secretions absorbed into the absorber 20 from leaking out. Coffee powder 16 is coated on the absorber 20.

That is, the coating layer 15 is not separately formed between the outer cover 10 and the absorber 20, but the coffee powder 16 is coated on the absorber 20, such that the pad can be made in a slim form.

In the preferred embodiment, the absorber 20 has a double-layer structure, and in this case, the coffee powder is coated between the absorber and the absorber, and then, the two absorbers are adhered together so as to prevent the coated material from leaking out.

In the preferred embodiments, oriental medicines which are generally used may be added to the coffee powder 16 in a fixed quantity, and then, the mixture is coated on the coating layer 15 or the absorber 20. Any oriental medicine can be used if the oriental medicine is harmless to humans and useful to humans. At least one among groups containing mugwort, cnidum, mint, dong quai, bluet and huttuynia cordata which are very effective to women can be used.

If the content of oriental medicines is more than percent of the entire coating materials, it halves the effects of coffee because the smell of oriental medicines is stronger than the smell of coffee.

Moreover, not the fruits but sweet-scented flowers, namely, flower powder or flower extracts may be mixed to the coffee powder 16, and then, the mixture may be coated on the coating layer 15 or the absorber 20.

For this, there are roses, chrysanthemums, azaleas, royal azaleas, magnolias, lilies, sunflowers, windflowers, crape myrtles, morning glories, bellflowers, daisies, daffodils, pansies, hyacinths, Verticillate Paris, violets, forsythias, cherry blossoms, dandelions, rape blossoms, *Rhododendron lateritiums*, carnations, cosmoses, wolfsbanes, *Strobilanthes oligantha* MIQ, and so on.

Figure 6:
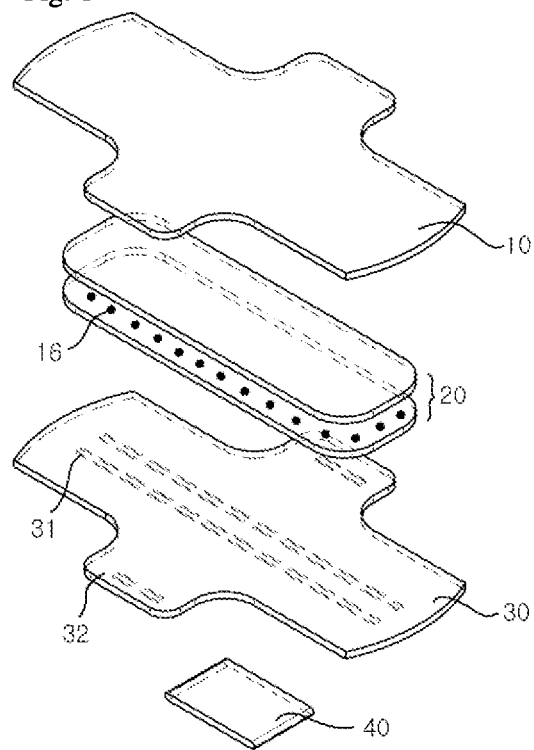
Figure 7:
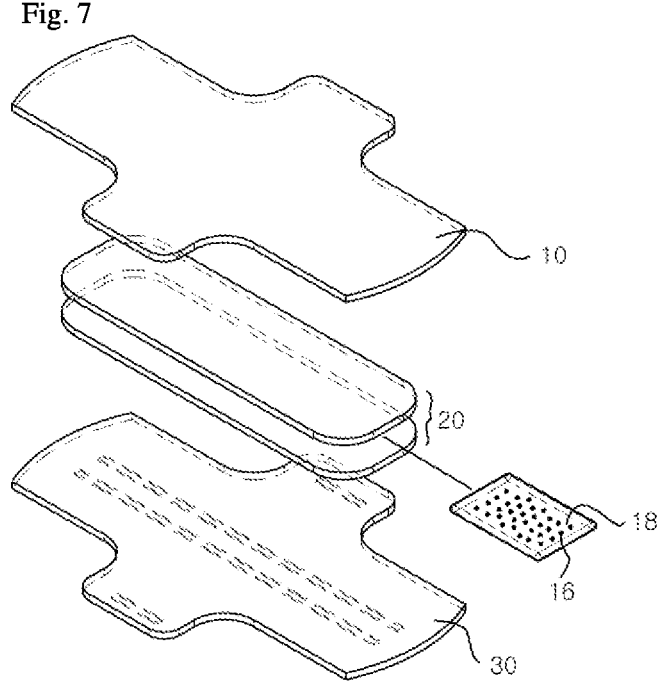

FIG. 6 is a view showing a pad coated with coffee according to a still further preferred embodiment of the present invention. In FIG. 6, a pack 18 contains coffee powder 16 or coffee extracts put between the absorbers 20. In this case, the pad according to the present invention can prevent that ingredients of the pack 18 from leaking out and provide deodorizing effects by coffee by emitting the smell of coffee when the pack 18 touches moisture.

In the above-mentioned embodiments, the coffee powder or the coffee extracts are coated only to general sanitary pads, but can be applied to the conventional mugwort steam pad or a conventional fumigation pad in the same way.

That is, the conventional mugwort steam pad or the conventional fumigation pad has a heating pack 40 detachably attached to the adhesion part 31 formed on the lower side of the waterproof outer cover 30, and the heating pack 40 can be separated when the user feels uncomfortable while using the pad in a state where the heating pack 40 is fixed to the lower side of the waterproof outer cover 30 because one side of the heating pack 40 is attached to the adhesion part 31 of the waterproof outer cover 30.

The pad coated with coffee according to the present invention can remove a bad smell by secretions, makes even users who dislike the smell of oriental medicines use the pad without avoidance and can be used widely to pad products which need deodorization, such as sanitary pads, mugwort steam pads and so on.

What is claimed is:

1. A pad coated with coffee which is used as hygienic goods, comprising:
   an outer cover (10);
   a coating layer (15) which is formed below the outer cover (10);
   an absorber (20) which is laid below the coating layer (15) to absorb liquid; and
   a waterproof outer cover (30) which is laid below the absorber (20) to prevent the liquid absorbed into the absorber (20) from leaking out, wherein coffee powder (16) is coated on the coating layer (15), and the coffee powder (16) is produced through the step of pulverizing dried coffee beans in 50 mesh size or less and is coated on the coating layer (15) together with an adsorbing material to enhance adherence of the pulverized coffee beans to the coating layer (15), thereby removing smells of the liquid and providing intrinsic functions of coffee.

2. A pad coated with coffee which is used as hygienic goods, comprising:

an outer cover (10);

an absorber (20) which is laid below the outer cover (10) to absorb liquid; and a waterproof outer cover (30) which is laid below the absorber (20) to prevent the liquid absorbed into the absorber (20) from leaking out, wherein coffee powder (16) is coated on the absorber (20), and the coffee powder (16) is produced through the step of pulverizing dried coffee beans in 50 mesh size or less and is coated on the absorber (20)) together with an adsorbing material to enhance adherence of the pulverized coffee beans to the absorber (20), thereby removing the smells of the liquid and providing intrinsic functions of coffee.

* * * * *